United States Patent
Philyaw

(10) Patent No.: US 6,365,108 B1
(45) Date of Patent: Apr. 2, 2002

(54) SILOXANE FILTER FOR O₂ SENSOR FOR BIO-GAS ENGINE

(75) Inventor: Dale A. Philyaw, Lafayette, IN (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 09/416,439

(22) Filed: Oct. 12, 1999

(51) Int. Cl.[7] .......................... B01D 46/10; B01D 41/04
(52) U.S. Cl. .......................... 422/98; 55/282.3; 55/283; 55/287
(58) Field of Search .................. 204/426, 427; 55/282.3, 16; 123/527; 429/13; 95/45; 422/98

(56) References Cited

U.S. PATENT DOCUMENTS

| | | | |
|---|---|---|---|
| 4,121,989 A | * 10/1978 | Shum et al. | 204/195 |
| 4,151,060 A | 4/1979 | Isenberg | 204/195 S |
| 4,323,440 A | 4/1982 | Akatsuka | 204/195 S |
| 4,717,464 A | * 1/1988 | Oshima et al. | 204/427 |
| 4,941,893 A | * 7/1990 | Hsieh et al. | 55/16 |
| 5,083,427 A | * 1/1992 | Anderson | 60/274 |
| 5,272,874 A | * 12/1993 | Paas | 60/297 |
| 5,335,492 A | * 8/1994 | Zirkel | 60/298 |
| 5,342,430 A | 8/1994 | Grocela-Kathe et al. | 75/746 |
| 5,400,590 A | * 3/1995 | Wagner et al. | 60/274 |
| 5,423,973 A | * 6/1995 | Friese et al. | 204/426 |
| 5,433,071 A | * 7/1995 | Willey et al. | 60/274 |
| 5,453,210 A | 9/1995 | Bardasz et al. | 252/18 |
| 5,489,319 A | * 2/1996 | Tokuda et al. | 96/400 |
| 5,503,657 A | * 4/1996 | Bouard et al. | 95/45 |
| 5,529,612 A | 6/1996 | Troost | 95/184 |
| 5,560,810 A | 10/1996 | Capetanopolous | 204/408 |
| 5,585,547 A | 12/1996 | Kim et al. | 73/31.05 |
| 5,660,940 A | * 8/1997 | Larsson et al. | 429/13 |
| 5,724,948 A | * 3/1998 | King et al. | 123/527 |
| 5,755,096 A | 5/1998 | Holleyman | 60/407 |
| 5,900,129 A | * 5/1999 | Tsuji et al. | 204/427 |
| 6,010,547 A | * 1/2000 | Jeong et al. | 55/282.3 |
| 6,036,829 A | * 3/2000 | Yamada et al. | 204/427 |

* cited by examiner

Primary Examiner—Jill Warden
Assistant Examiner—Brian J. Sines
(74) Attorney, Agent, or Firm—Fred J. Baehr; Alan J. Hickman

(57) ABSTRACT

A siloxane filter system for protecting an oxygen probe utilized in an internal combustion engine fueled by bio-gases, the filter system having a stainless fiber filter removably disposed in a housing having and inlet port and an outlet port disposed in fluid communication with an exhaust duct in such a manner as to cause exhaust gases to flow through the housing and filter, the oxygen probe is disposed in the housing down stream of the filter, causing siloxane in the exhaust gases to be deposited on the stainless fibers of the filter and essentially siloxane free gases passes over the oxygen probe extending its useful life.

10 Claims, 3 Drawing Sheets

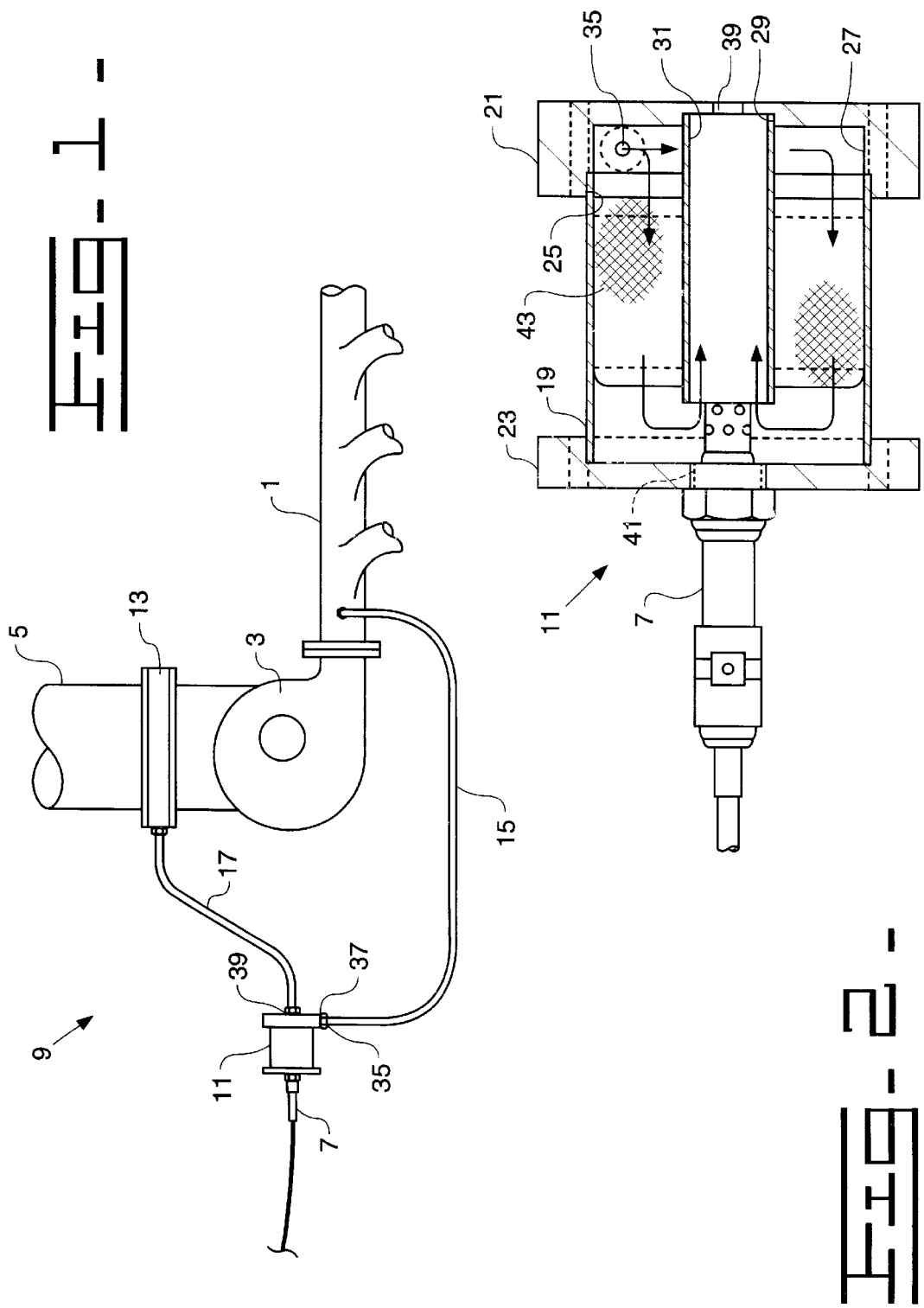

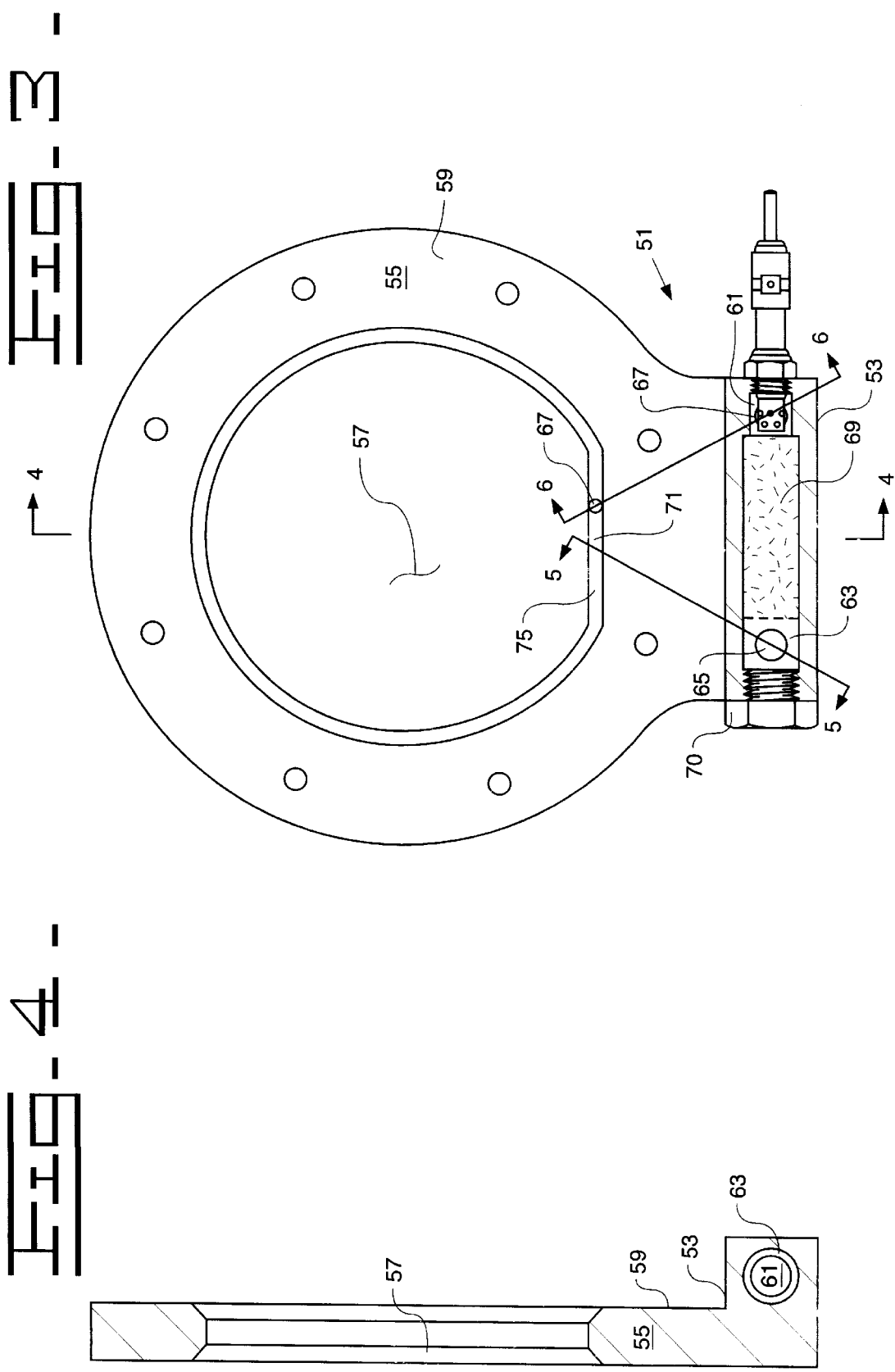

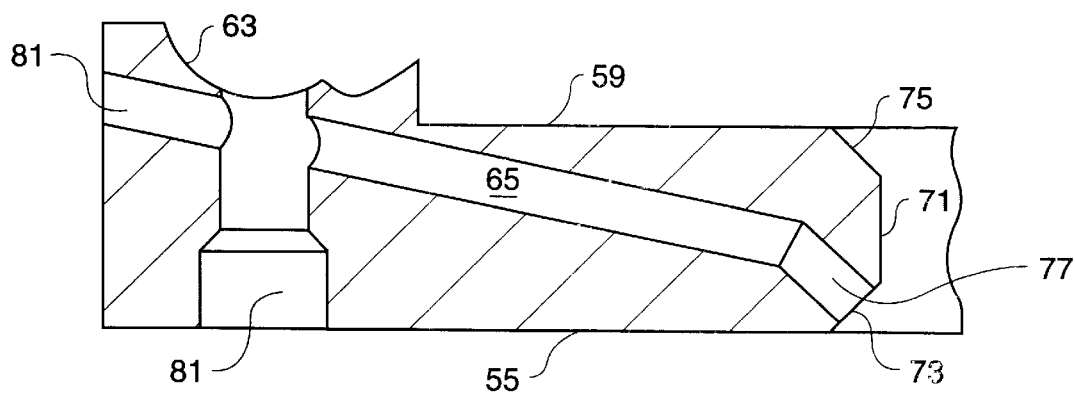
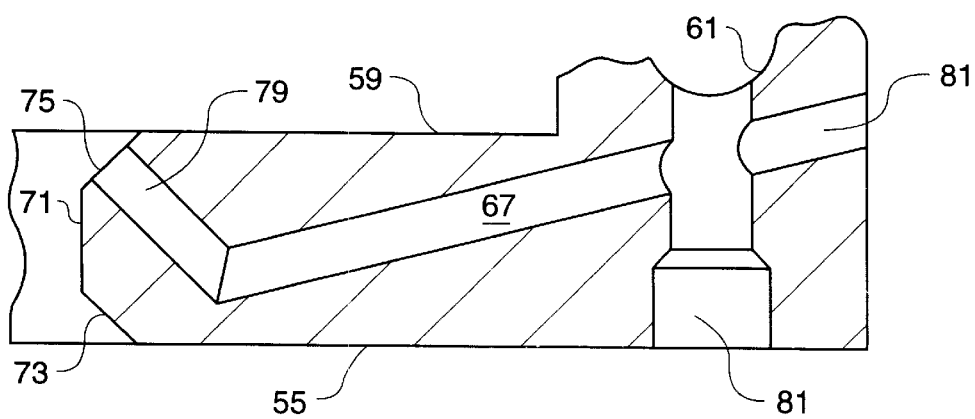

SILOXANE FILTER FOR O₂ SENSOR FOR BIO-GAS ENGINE

TECHNICAL FIELD

The invention relates to a filter and more particularly to a siloxane filter for preconditioning exhaust gases delivered to an oxygen probe sensor for an internal combustion engine fueled by bio-gas gasses resulting from organic decomposition.

BACKGROUND ART

Gaseous silicon compounds, siloxane, are common components found in bio-gas fuels produced in land fills and digesters. When burned as fuel in an internal combustion engine siloxane deposits are formed on all engine and exhaust system surfaces that come in contact with the exhaust gases. Among other problems these deposits will render engine oxygen probes useless after a short time interval. The oxygen sensor probe is a devise that samples the percent of oxygen remaining in the engine exhaust gases after combustion. It generates an electrical signal, which in turn is used to control engine air and fuel mixture assuring proper emissions, while preventing pre-ignition and/or detonation.

DISCLOSURE OF THE INVENTION

In general, a siloxane filter system for protecting an oxygen probe used in an internal combustion engine that burns bio-gases, when made in accordance with this invention, comprises a stainless steel or other fiber filter removably disposed in a housing. The housing has an inlet port and an outlet port disposed in fluid communication with an exhaust duct in such a manner as to cause exhaust gases to flow through the housing and over the filter. The oxygen probe is disposed in the housing down stream of the filter, causing siloxane in the exhaust gases to be deposited on the stainless steel or other fibers of the filter and essentially siloxane free gases passes over the oxygen probe extending its useful life.

BRIEF DESCRIPTION OF THE DRAWINGS

The invention as set forth in the claims will become more apparent by reading the following detailed description in conjunction with the accompanying drawings, wherein like reference numerals refer to like parts throughout the drawings and in which:

FIG. 1 is a schematic view of an exhaust manifold, turbocharger, and exhaust duct for an internal combustion engine that burns bio-gas having a siloxane filter for an oxygen probe;

FIG. 2 is a sectional view of the filter;

FIG. 3 is a partial sectional view of a plate that is disposed in the exhaust duct and has a filter for the oxygen probe disposed therein;

FIG. 4 is a sectional view taken on line IV—IV of FIG. 3;

FIG. 5 is a sectional view taken on line V—V of FIG. 3; and

FIG. 6 is a sectional view taken on line VI—VI of FIG. 3.

BEST MODE FOR CARRYING OUT THE INVENTION

Referring now to the drawings in detail and in particular to FIG. 1, there is shown an exhaust manifold 1, turbocharger 3 and exhaust duct 5 for an internal combustion engine (not shown) that uses bio-gasses as a fuel. The bio-gasses contain gaseous silicon compounds, commonly referred to as siloxane, which deposit on all engine and exhaust system surfaces exposed to exhaust gases. An oxygen probe 7 is disposed in a siloxane filter system 9 which removes the siloxane from the exhaust gasses before they flow over the oxygen probe 7. The oxygen probe 7 produces an electrical signal proportional to the amount of oxygen in the exhaust gases. An electronic control module (not shown) utilizes the signal from the oxygen probe 7 to regulate the fuel and air ratio and thereby control the engine emissions within a specified range while preventing pre-ignition and or detonation. The filter system 9 further comprises a housing 11 and an orifice plate 13 disposed in the exhaust duct 5. An inlet conduit 15 provides fluid communication between the housing 11 and the exhaust manifold 1. An outlet conduit 17 provides fluid communication between the housing 11, orifice plate 13 and the exhaust duct 5.

Referring now to FIG. 2 in detail the siloxane filter system 9 comprises the housing 11 having an outer cylindrical portion 19 disposed between two end plates 21 and 23. The end plates 21 and 23 are bored to receive the outer cylindrical portion 19. One of the end plates 21 has four bores the largest bore 25 receives the outer cylindrical portion 19. The second largest bore 27 has a diameter generally equal to the inside diameter of the outer cylindrical portion 19. The next smaller bore 29 has a diameter that receives an inner cylindrical portion or tube 31. The inner cylindrical portion does not extend to the other end plate 23. An inlet port 35 is disposed in fluid communication with the second largest bore 27. The inlet port 35 is so disposed in one side 37 of the one end plate 21 to cause the influent exhaust gasses to swirl in the second largest bore 27. The smallest bore forms an outlet port 39. The other end plate 23 has a central threaded opening 41 for receiving the oxygen probe 7. A stainless steel fiber filter 43 is disposed in the housing 11 between the inner and outer cylindrical members 19 and 31. The swirling exhaust gasses in the second largest bore 27 are distributed evenly to the filter 43 to provide proper filtering of siloxane from the exhaust gases as they pass through the filter 43 before they contact the oxygen probe 7. The end plates 21 and 23 are held tightly against the outer cylindrical portion 19 by through bolts or other means (not shown).

Referring now to FIG. 3 in detail there is shown an alternate embodiment in which a filter housing 51 is disposed in an enlarged portion 53 of a plate 55. The plate 55 is disposed in the exhaust duct and has an opening 57 that generally mates with the opening in the exhaust duct (not shown in this figure). The enlarged portion 53 extends above a major top surface 59 of the plate 55. The enlarged portion 53 of the plate 55 has a hole 61 bored through the enlarged portion 53 and a counter bored hole 63 on one end of the hole 61. An inlet port 65 is disposed in fluid communication with the originating end of the counter bored hole 63. An outlet port 67 is disposed in fluid communication with the bored hole 61. A stainless steel fiber filter element 69 is disposed in the counter bore 63 and the oxygen probe 7 is disposed in the hole 61. A threaded plug 70 is disposed in the open end of the counter bored hole 63 to close it off and to provide for easy replacement of the filter element 69.

Referring now to FIG. 4, the counter bore 63 is disposed above the upper main surface 59 of the plate 55. The opening 57 in the plate 55 that mates with the opening in the exhaust duct has a portion 71 that protrudes into the exhaust duct. The protruding portion 71 has a beveled portion 73 on the upstream side of the protrusion 71 and a beveled portion 75 on the downstream side of the protrusion 71.

Referring now to FIG. 5 the inlet port 65 originates in the upstream beveled portion 73 of the protruding portion 71 and extends to the counter bored hole 63. A portion 77 of the inlet port 65 is perpendicular to the upstream beveled portion 73 of the protruding portion 71. The inlet port 65 is sloped downwardly to allow water to drain therefrom. The inlet port 65 is formed by drilling three intersecting holes in the plate 55 and the enlarged portion 53. Two of the drilled holes have a plug 81 disposed in the open end to form a seal.

Referring now to FIG. 6 the outlet port 67 terminates in the downstream beveled portion 75 of the protruding portion 71 and extends to the bored hole 61. A portion 79 of the outlet port 67 is perpendicular to the down stream beveled portion 75. The outlet port 67 is formed by drilling three intersecting holes in the plate 55 and the enlarged portion 53. Two of the drilled holes have the plug 81 disposed in the open end to form a seal.

This embodiment has the advantage of being very close to the exhaust duct so that typical exhaust gas contaminates of pressure, temperature and condensate have very little affect on the oxygen probe functionally and is therefore useful on any internal combustion utilizing oxygen probes to control air fuel ratios. The location of the inlet and outlet ports 65 and 67 in the beveled portions 73 and 75 of the protruding portion 71 cooperate to generally operate as a pitot tube to provide that the optimum amount of filtered exhaust gasses pass over the oxygen probe 7 to extend its useful life.

While the preferred embodiments described herein set forth the best mode to practice this invention presently contemplated by the inventor, numerous modifications and adaptations of this invention will be apparent to others of ordinary skill in the art. Therefore, the embodiments are to be considered as illustrative and exemplary and it is understood that the claims are intended to cover such modifications and adaptations as they are considered to be within the spirit and scope of this invention.

Industrial Applicability

A siloxane filter system made in accordance with this invention advantageously provides the optimum amount of filtered exhaust gases to the oxygen probe to increase the time between filter changes and easy replacement of the filter element when it becomes saturated with siloxane deposits.

What is claimed is:

1. A siloxane filter system for protecting an oxygen probe utilized in an internal combustion engine having an exhaust duct and being fueled by landfill gases, the siloxane filter system comprising a fiber filter removably disposed in a housing, the housing having an outer cylindrical portion disposed between two end plates bored to receive the outer cylindrical portion, one of the end plates having four bores the largest bore receiving the outer cylindrical portion the second largest bore having a diameter generally equal to the inside diameter of the outer cylindrical portion and the next smaller bore having a diameter that receives an inner cylindrical portion that does not extend to the other end plate, an inlet port and an outlet port disposed in fluid communication with the exhaust duct in such a manner as to cause exhaust gases to flow through the housing and filter, the outlet port being disposed in fluid communication with the second largest bore and the inlet port being so disposed in a side of the one end plate to cause the influent exhaust gasses to swirl in the second largest bore, the other end plate having a central threaded opening for receiving the oxygen probe and the fiber filter being disposed in the housing between the inner and outer cylindrical members filtering the exhaust gases of siloxane prior to contacting the oxygen probe, whereby siloxane in the exhaust gases is deposited on the fibers of the filter and essentially siloxane free gases pass over the oxygen probe, extending its useful life.

2. A siloxane filter system for protecting an oxygen probe utilized in an internal combustion engine having an exhaust duct and being fueled by bio-gases, the siloxane filter system comprising a plate disposed in the exhaust duct and having an opening that generally mates with the opening in the exhaust duct and an enlarged portion on one side of the plate having a large bore therein forming a housing, a fiber filter removably disposed in the housing, the housing having and inlet port and an outlet port disposed in fluid communication with the exhaust duct in such a manner as to cause exhaust gases to flow through the housing and filter, the oxygen probe being disposed in the housing down stream of the filter, whereby siloxane in the exhaust gases is deposited on the fibers of the filter and essentially siloxane free gases passes over the oxygen probe extending its useful life.

3. A siloxane filter system as set forth in claim 2, wherein the counter bore is above the main portion of the plate.

4. The siloxane filter system as set forth in claim 3, wherein the opening in the plate that mates with the opening in the exhaust duct has a portion that protrudes into the opening and the inlet and outlet ports, respectively, originate and terminate in the protruding portion.

5. The siloxane filter system as set forth in claim 4, wherein the protruding portion is beveled on both upstream and downstream sides.

6. The siloxane filter system as set forth in claim 5, wherein the inlet port originates in the upstream bevel and the outlet port terminates in the downstream bevel.

7. The siloxane filter system as set forth in claim 6, wherein a portion of the inlet port and a portion of the outlet port is generally perpendicular to the associated bevel on the protruding portion whereby the inlet and outlet ports act in combination to provide the correct flow of filtered gas over the oxygen probe.

8. The siloxane filter system as set forth in claim 7, wherein the inlet port is sloped downwardly to allow water to drain from the inlet port.

9. The siloxane filter system as set forth in claim 8, wherein the inlet port is sloped downwardly to allow water to drain from the inlet port.

10. The siloxane filter system as set forth in claim 9, wherein the filter fibers are stainless steel.

* * * * *